United States Patent [19]

Fahy

[11] Patent Number: 4,559,298

[45] Date of Patent: Dec. 17, 1985

[54] CRYOPRESERVATION OF BIOLOGICAL MATERIALS IN A NON-FROZEN OR VITREOUS STATE

[75] Inventor: Gregory M. Fahy, Rockville, Md.

[73] Assignee: American National Red Cross, Washington, D.C.

[21] Appl. No.: 444,057

[22] Filed: Nov. 23, 1982

[51] Int. Cl.$^4$ ............................. A01N 1/02; F25C 1/00
[52] U.S. Cl. ............................................. 435/1; 62/67; 62/78; 435/240; 435/241
[58] Field of Search .................... 62/67, 78; 435/1, 2, 435/240, 241

[56] References Cited

U.S. PATENT DOCUMENTS 3,677,024  7/1972  Segall ........................................ 62/64
3,940,943  3/1976  Sikes ......................................... 62/64

OTHER PUBLICATIONS

MacFarlane et al.—*Cryo-Letters* 2, 353–358 (1981).
Fahy et al.—*Cryobiology*, vol. 21 (1984) pp. 407–426.
*Cryonics*, Issue No. 12, Jul. 1981.
Abstract: Fahy, VII International Biophysics Congress and PanAmerican Biochemistry Congress, Mexico City, Aug. 23–28, 1981.
Abstract: Fahy, The Transplantation Society, Cambridge, England Apr. 6–9, 1981.
Abstract: Fahy, Society for Cryobiology, St. Louis, Missouri Jun. 14–18, 1981.
Note: Cryobiology 18: 617, 1981 (Fahy).

*Primary Examiner*—Sam Rosen
*Attorney, Agent, or Firm*—Holman & Stern

[57] ABSTRACT

A method is provided for the successful cryopreservation of biological materials including whole organs, organ sections, tissues and cells, in a non-frozen (vitreous) state, comprising cooling the biological material to be preserved under pressure in the presence of a non-toxic vitrifable protective solution to at least the glass transition temperature thereof to vitrify the solution without substantial nucleation or ice crystal growth and without significant injury to the biomaterial. The invention also provides non-toxic protective vitrification solutions useful in the cryopreservation of biomaterials.

18 Claims, 5 Drawing Figures

CRYOPRESERVATION OF BIOLOGICAL MATERIALS IN A NON-FROZEN OR VITREOUS STATE

BACKGROUND OF THE INVENTION

The low temperature preservation of biological tissues and organs has been the subject of much research effort. Although organ banks similar to blood banks would have great medical utility, it has not been possible to successfully preserve clinically required whole organs or certain tissue sections by cryogenic methods. Organized tissues and organs, especially the heart and kidney, are particularly susceptible to mechanical damage from ice crystals formed during freezing. Efforts to protect tissues from damage during freezing have involved the use of chemicals known as cryoprotective agents which frequently become excessively concentrated during the freezing process and prove toxic to the biological material. In order to avoid damage caused by ice formation on freezing, methods have also been developed which employ solutes in amounts sufficient to greatly depress the freezing point of aqueous protective solutions, permitting the tissues or organs to be stored at low temperatures in a liquid state. Typical of such methods is the equilibrium method employed by Farrant (*Nature*, 205:1284-87, 1965) wherein the tissue or organ is incubated with a penetrating cryoprotectant such as dimethyl sulfoxide (DMSO) until the intra- and extracellular concentrations of DMSO are equilibrated. The concentration of DMSO is gradually increased and the temperature simultaneously gradually lowered without freezing until a sufficiently low temperature is obtained. Owing to the necessity of equilibrating DMSO across the cell membranes with restoration of isotonic volumes, while lowering the temperature, the process is very slow. Further, in order to sufficiently depress the freezing point of the preservation solution, very high concentrations of DMSO are necessary and must be introduced and removed at the subzero temperatures contemplated. Additionally, the same slow procedure must be employed in reverse on recovery (warming) of the tissue for use.

Accordingly, it is desirable to provide a method for the successful preservation of organs, tissues and other biological materials at very low temperatures which avoids the formation of ice crystals, minimizes the effective concentration of potentially harmful chemicals, and permits the rapid introduction and removal of cryoprotectants at feasible temperatures, without the necessity of elaborate equipment to monitor precise conditions of concentration and temperature. These advantages are obtained by the vitrification process of the present invention.

The principles of vitrification are well-known. Very generally, the lowest temperature a solution can possibly supercool to without freezing is the homogeneous nucleation temperaure $T_h$, at which temperature ice crystals nucleate and grow, and a crystalline solid is formed from the solution. Vitrification solutions have a glass transition temperature $T_g$, at which temperature the solution vitrifies, or becomes a non-crystalline solid, higher than $T_h$. Owing to the kinetics of nucleation and crystal growth, it is effectively impossible for water molecules to align for crystal formation at temperatures much below $T_g$.

On cooling most dilute aqueous solutions to the vitrification temperature (about $-135°$ C.), $T_h$ is encountered before $T_g$, and ice nucleation occurs, which makes it impossible to vitrify the solution. In order to make such solutions useful in the preservation of biological materails by vitrification, it is therefore necessary to change the properties of the solution so that vitrification occurs instead of ice crystal nucleation and growth. While it is known that many solutes, such as commonly employed cryoprotectants like dimethyl sulfoxide (DMSO), raise $T_g$ and lower $T_h$, solution concentrations of DMSO or similar solutes high enough to permit vitrification typically approach the eutectic concentration and are generally toxic to biological material. While it is also generally known that high hydrostatic pressures similarly raise $T_g$ and lower $T_h$, vitrification of most dilute solutions by the application of pressure is either impossible or impractical. Further, for many solutions vitrifiable by the application of pressure, the required pressures cause unacceptably severe injury to unprotected biomaterials during vitrification thereof; for example, a pressure of only 1000 atm is lethal to unprotected kidney slices. These and other barriers to cryopreservation of biological materials have not been surmounted in the prior art.

A summary of the effects of increasing concentrations of solute at decreasing temperatures on the cryobehavior of an exemplary solution at two (2) different pressures is presented in the graph in FIG. 1 ($T_m$ is the melting point or liquidus temperature of the solution).

SUMMARY OF THE INVENTION

According to the present invention, a method is provided for the successful cryopreservation of biological materials including whole organs, organ sections, tissues and cells, in a non-frozen (vitreous) state. The method comprises cooling the biological material to be preserved under pressure in the presence of a non-toxic vitrifiable protective solution to at least the glass transition temperature thereof to vitrify the solution without substantial nucleation or ice crystal growth and without significant injury to the biomaterial. This vitrification process explicitly takes advantage of the non-equilibrium behavior of concentrated aqueous solutions so that a minimal concentration of toxic penetrating cryoprotectant is required while freezing (formation of ice crystals) is suppressed. Thus, both mechanical and chemicl damage to the biological systems is obviated.

The invention further provides non-toxic protective vitrification solutions useful in the cryopreservation of biomaterials according to the present invention comprising a mixture of glass-forming solutes in aqueous solution. The vitrification solutions are vitrifiable under biocompatible pressure conditions, and, under vitrification conditions, are non-toxic and effectively protect the biological material from injury due to exposure to cold (cryoprotection) and high pressure (baroprotection).

DETAILED DESCRIPTION OF THE INVENTION

Figure 1:
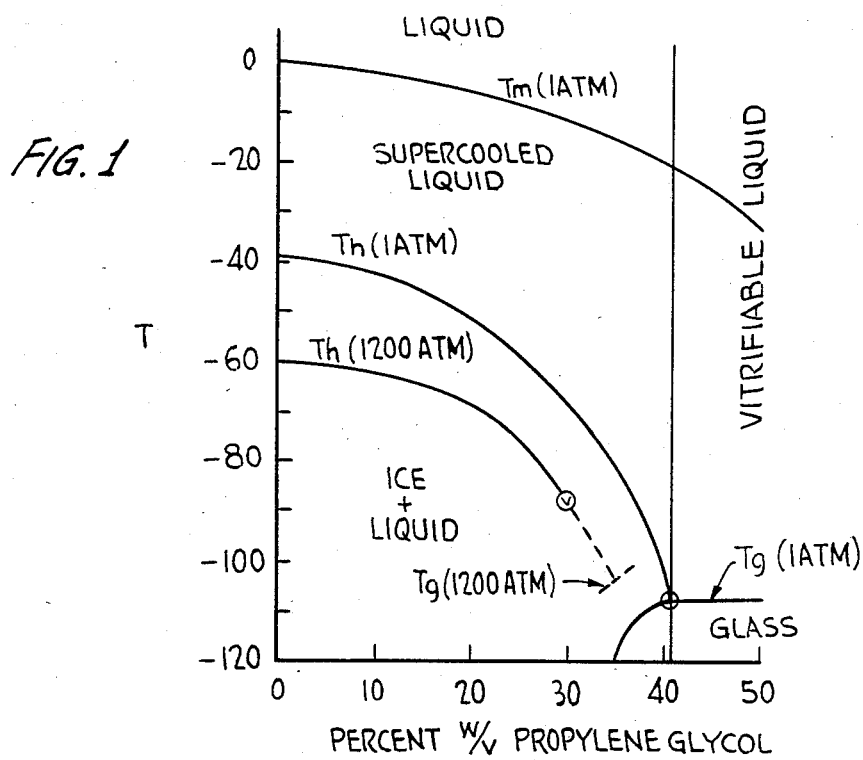

Broadly, the vitrification process of the invention comprises cooling the biological system to be cryoprotected to between about 0° C. and 10° C., and introducing a dilute vitrification solution, usually by vascular perfusion for organs. The solution concentration is gradually increased to the concentration needed for vitrification, and the temperature simultaneously lowered several degrees if the solution is potentially toxic.

Unlike prior art methods, in the present process the rate and duration of solution introduction should not permit the cells of the material to re-establish their isotonic volume prior to vitrifying. Instead, the introduction of vitrification solution should proceed relatively rapidly, and should be terminated when an equilibrium concentration of solutes across the cell membrane is established as a result of depletion of intracellular fluids, rather than as a result of full permeation of cells by protective solution. The cell volume is desirably reduced to between about one-third and two-thirds of normal, with an intracellular solute concentration of at least about 30%, which permits rapid delivery of protective material to the biological material as well as a rapid removal of recovery. The time required for delivery, usually about 1 to 2 hours in the case of an organ, is much faster than would be required using conventional criteria for equilibration thereby reducing the danger of solute toxicity. Known protocols for increasing concentration over time during perfusion are generally applicable (with modification), particularly the Levin protocol (*Cryobiology*, 18:617–618, 1981); the Pegg protocol (*Cryobiology*, 14:168–178, 1977); the Collins protocol (Collins, personal communication, 1982); the Segal protocol (*Cryobiology*, 19:41–49, 50–60, 1982); step protocols (e.g., *Cryobiology*, 17:371–388, 1980) or various biologically acceptable combinations thereof.

Upon completion of solution introduction, the biomaterial is immediately transferred to a high pressure chamber, bathed in a non-toxic fluid, and protected from contact with the fluid used to induce hydrostatic pressures. The pressure is raised quickly to the vitrification pressure and the temperature lowered rapidly to about 5° C. to 15° C. below $T_g$, the glass transition temperature at 1 atm for the vitrification solution employed. Cooling much below $T_g$ at high pressure causes cracking of the glass (vitrifracture), and must be avoided. The rapidity of pressure application and temperature reduction is important in order to prevent or minimize both the toxic effect of the glass-forming solutes and any baroinjury; pressurization rates up to about 500 atm/min are generally not injurious. Upon reaching the final temperature, the pressure is released and the material removed from the chamber. Storage may be either at approximately $T_g$ minus 15° C. or at about −196° C., depending upon the difficulty of avoiding vitrifracture.

To retrieve the biological material from storage, the vitrified material is warmed at a heating rate sufficient to avoid devitrification (formation of ice crystals) which is damaging to the material. Heating rates of about 150° C. to about 600° C. $\min^{-1}$ are generally sufficient at the solution concentrations contemplated, with the lower rates applicable to higher concentrations. If the glass is "doubly unstable" ($T_h$ higher than $T_g$ at 1 atm), pressure application during rewarming is essential to make $T_g > T_h$ and thereby to avoid formation of ice crystals, and faster warming rates, for example 500°–1000° C./min, may also be necessary. A summary of the effects of various heating rates on the temperature at which several successfully vitrified solutions devitrify on warming ($T_c$) and the temperature at which the solutions become vitreous ($T_g$) is graphically presented in FIGS. 3–4. Microwave or induction heating is suitable.

The invention is predicated on the discovery that the high solution concentration of toxic penetrating glass-forming agents such as DMSO necessary to achieve a vitrifiable solution (about 49% DMSO) can be reduced by employing instead a vitrification solution comprising an admixture of solutes in aqueous solution, and vitrifying the solution under biocompatible hydrostatic pressures, typically from about 0.2 kbar to about 2 kbar, depending on the exact composition of the solution and the cooling rate. If the solute system components, their concentration, and the operating pressure are well-chosen, the solution will vitrify at non-toxic solute system concentrations and biocompatible pressures. The concentration of toxic glass-forming materials required for vitrification is further reduced if the introduction of vitrification solution is controlled as previously described so that the cells are below isotonic volume prior to vitrification. The shrunken cells thus have an effectively increased intracellular protein concentration, which further reduces the amount of penetrating glass-former needed for intracellular vitrification.

The vitrification solutions of the invention must be vitrifiable at biocompatible pressures, usually under about 2000 atm, depending upon the baroprotection afforded by the solute system and the particular application. The pressure required to vitrify is dependent on the concentration of the vitrification solution, and the vitrification solutions must not be toxic under vitrification conditions employed. Thus, vitrification solutions useful in the process of the invention must be conformed to these parameters.

Useful vitrification solutions according to the invention are aqueous solutions of solutes characterized by the ability to form glasses at biocompatible concentrations and pressures, and by the ability to penetrate the cells of the biomaterial sufficiently to effect intracellular vitrification, without formation of ice crystals. While a single solute may perform these functions for some applications, vitrifiable solutions comprising a single glass-forming penetrating solute (such as the 49% DMSO solution mentioned supra) are generally too toxic to be used with sensitive tissues and cells, for example those derived from the kidney.

Suitable penetrating glass-forming solutes (PGF) for use in the vitrification solutions of the invention include dimethyl sulfoxide (DMSO), glycerol, ethylene glycol, and propylene glycol (PG). To decrease toxicity of PGF systems, a high or low molecular weight non-penetrating glass-former (NPGF) is included in the system, for example polyvinylpyrrolidone (PVP), hydroxyethyl starch (HES), HAEMACCEL (available from Hoechst Pharmaceuticals), sucrose, proteins, or other colloids. While the glass-formers in appropriate concentrations generally also function as baroprotectants, additional solutes which enhance baroprotection may be included, if desired. Other solutes which may be included are those, for example, which counter the effects of toxic materials present such as DMSO; known compounds which block DMSO toxicity include amides such as acetamide (AA), sulfamide, glycineamide, formamide, and urea. Membrane and protein stabilizers may also be employed to counter solute toxicity.

Particularly suitable solute systems for many applications include mixtures of DMSO, AA, PG and PVP in concentrations totalling about 41–51% w/v.

Vitrification of the protective solutions of the invention occurs at a critical solution concentration (vitrification concentration) for a given pressure. Since the vitrification concentration (VC) varies inversely with the pressure applied to the protective solution, by application of pressure, the VC of a particular protective solution is reduced. In general, at 1000 atm the vitrification concentration is about 5% w/v lower than the VC at 1 atm (see Table I). Based on limited data, VC may generally be expected to decrease at a greater rate with increase in pressure above 1000 atm (PG in Table I). Anomalous behavior of solutions under the pressures contemplated occasionally occurs, however. Additionally, the presence of some solutes, such as the aforementioned amides, may tend to increase the VC, rather than lower it.

The vitrification concentration is obtainable by reference to an appropriate supplemented phase diagram. The phase diagrams are developed by determining the temperature dependence of various phase changes as a function of conditions, as is well-known in the art. Alternatively, vitrification characteristics of a particular solution can be determined by the simple expedient of chilling. In general, the concentration of penetrating glass-former in the vitrification solution is equal to or less than the concentration required for vitrification at 1 atm plus about 10%, the extra 10% being necessary to suppress devitrification at slow warming rates. Practically, the upper bound on PGF will depend on the solute system employed, pressure applied, and the cooling rate, inter alia. Concentrations of PGF as low as 30% are contemplated at about 2000 atm, with very fast cooling and significant amounts of non-penetrating GF, if limited nucleation and very limited crystal growth is acceptable, as for example in biological microscopy applications. The cooling rate is inversely related to the amount of pressure needed to vitrify a given solution, and an increase in cooling rate from about 10° K. min$^{-1}$ to about 100° K. min$^{-1}$ decreases vitrification pressure (VP) (the pressure needed to vitrify) by about 100 atm for average solutions. Since VP is directly related to VC, manipulation of the cooling rate will permit VC or VP to vary accordingly. This is useful if, for example, baroprotection is incomplete at VP; the cooling rate can then be increased, and VP lowered. Similarly, if VC is toxic, VC can be reduced by increasing the cooling rate and holding VP steady. Cooling rates of about 10° K. min$^{-1}$ are easily attainable, and rates within the range of about 5° K. min$^{-1}$ to about 50° K. per minute are generally contemplated; however, much higher cooling rates of up to several thousand degrees per minute are possible in smaller biological systems.

In addition to being vitrifiable at biocompatible pressures, the protective solutions must be both biologically innocuous and protect against baroinjury under vitrification conditions.

Table II summarizes results from numerous studies of solute toxicity. The system investigated is tissue from the cortex of the rabbit kidney; the viability index is the ability of the tissue to re-establish a normal K$^+$:Na$^+$ ratio upon removal of the glass-former and warming to 25° C. As can be seen, DMSO and DMSO+propylene glycol are non-toxic at a total concentration of 30% w/v. Addition of 6% PVP K30 to 15% DMSO+15% PG (data not shown) does not significantly increase the toxicity of this mixture. The toxicity of DMSO and of DMSO+PG rises quite rapidly as the total concentration is raised to 40%. This toxicity can be mitigated by lowering the temperature, by using acetamide or urea to block the biochemical effects of DMSO, and by reducing the time of exposure to the glass-former. Mutual dilution of glass-formers may be helpful (Group D vs. Group E), and may be ineffective (Groups K–M). Further, the toxicity neutralizers (acetamide and urea) elevate the concentration of glass-former necessary for vitrification (Table I).

Figure 2:
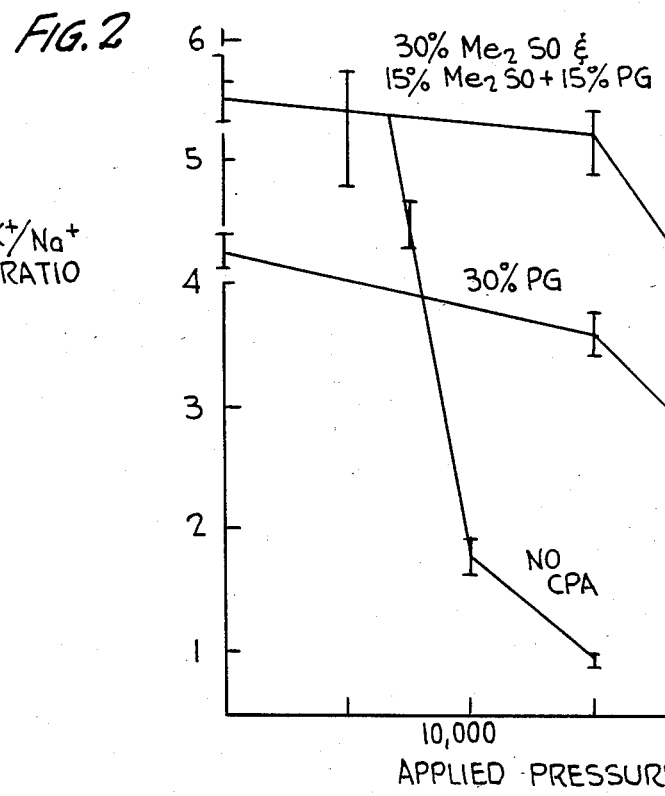

The effect of baroprotective solutes on the pressure tolerance of kidney tissue is set forth in FIG. 2. As is apparent from the graph, untreated tissue ("NO CPA") failed to tolerate 10,000 psi (685 atm) whereas tissue treated with 30% DMSO or 30% (DMSO+PG) were undamaged at 1030 atm; but failed to tolerate 23,000 psi. The samples (I) were exposed to the test pressures for 20 minutes, which represents a typical exposure time to pressure according to the process of the invention, including both vitrification and warming under pressure.

TABLE I

PREVENTION OF CRYSTALLIZATION AT ONE AND 1000 ATM[1]

| PENETRATING GLASS FORMERS (PGF) | CRITICAL CONCENTRATION TO VITRIFY AT | | | |
|---|---|---|---|---|
| | ONE ATM | | 1000 ATM | |
| | 10 moles (Q) moles | % w/v | 10 moles (Q) moles | % w/v |
| Ethylene glycol | 3.2 | 55 | 2.6 | 49 |
| 1,3-Propanediol | 2.9–3.1 | 56–58 | — | — |
| Glycerol | 2.7 | 65 | 2.3 | 60 |
| DMSO | 2.1 | 49 | 1.8 | 45 |
| 1,2-Propanediol (PG)[2] | 1.8 | 43.5 | 1.4 | 38.5 |
| 2,3-Dihydroxybutane | 1.7 | 46 | — | — |
| Trimethylamine-acetate (TMAA) | 1.1 | 41 | ~0.86 | ~36 |
| Dimethylamino-ethylacetate | 1.0 | 45 | ~0.88 | ~42 |
| PGF MIXTURES | | | | |
| DMSO + urea (3 g:1 g) | 3.0 | 59 | ~3.6 | ~55 |
| DMSO + acetamide (DA) (1 mole:1 mole) | 2.8 | 53 | 2.3 | 48.5 |
| DA + PG (1 g:1 g) (DAP) | ~2.3 | ~50 | ~1.9 | ~45 |
| DMSO + PG (DP) (1 g:1 g) | 1.9 | 46 | 1.6 | 42 |

| MIXTURES OF PGF AND NON-PENETRATING GLASS-FORMERS (NPGF) % (w/v) | CRITICAL CONCENTRATION TO VITRIFY AT | | | |
|---|---|---|---|---|
| | ONE ATM | | 1000 ATM | |
| | 10 moles (Q) | % w/v[3] | 10 moles (Q) | % w/v[3] |
| DA + 6 PVP | 2.2 | 45.5 | 2.0 | 42.5 |
| DMSO + 6 PVP | 2.0 | 46 | 1.5 | 41 |
| DAP$_{10}$[4] + 6 PVP | 2.2 | 46 | 1.8 | 40 |
| DAP$_{10}$ + 8 PVP | — | — | 1.7 | 39 |
| DAP$_{10}$ + 6 HES | 2.4 | 49 | 1.9 | 42 |
| DAP$_{10}$ + 6 Trehalose | — | — | — | ~43 |
| DAP$_{10}$ + 6 Sucrose | ~2.3 | ~47 | 1.9 | 42 |
| DA + 6 Sucrose | 2.5 | ~49 | 2.2 | 45 |
| DA + 6 HES | 2.5 | 50 | 2.0 | 44 |

[1]Determination made on bulk (8 ml) samples cooled at apporoximately 10° C./min to T$_g$, in the presence of ~300 moles base perfosate.
[2]Concentration needed to vitrify at 1200 atm equals 30% w/v.
[3]% w/v of PGl (not including amount of NPGF in mixture).
[4]DMSO + acetamide (1 mole:1 mole) plus 10% w/v PG.

Figure 5:
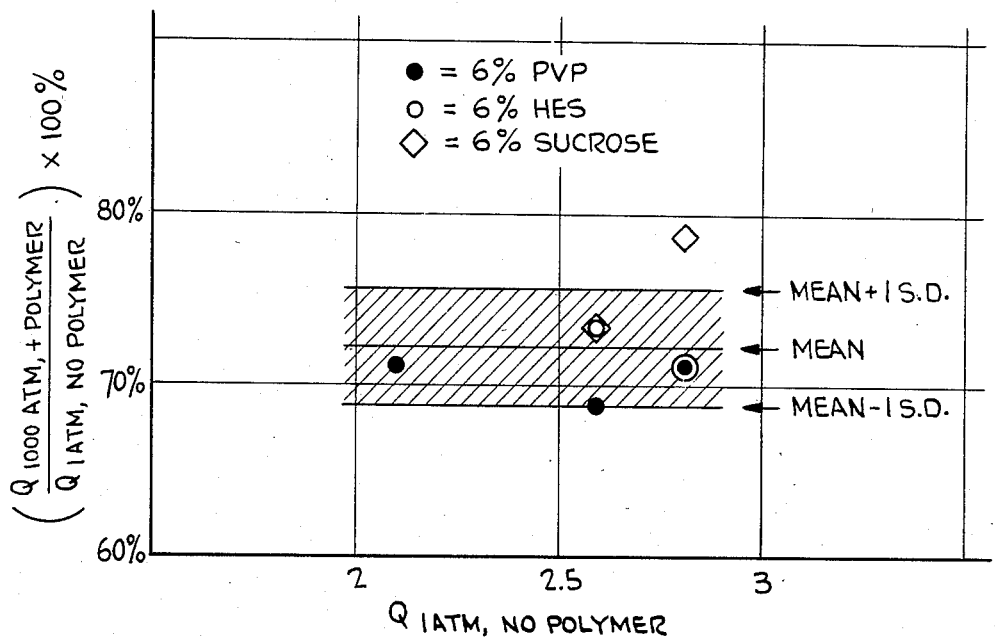

A summary of the combined effects of pressure and presence of non-penetrating glass-former on the concentration of penetrating glass-former needed to vitrify is presented in graphic form in FIG. 5.

TABLE II
EFFECT OF GLASS-FORMER CONCENTRATION ON KIDNEY SLICE VIABILITY*

| GROUP | GLASS-FORMER CONCENTRATIONS (% w/v) | n | K+:Na+ | p | VS. |
|---|---|---|---|---|---|
| A | Controls (No Glass-Former) | 7 | 5.7 ± .3 | — | — |
| B | 30% DMSO | 5 | 5.6 ± .3 | NS | A |
| C | 15% DMSO + 15% PG | 5 | 5.6 ± .1 | NS | A,B |
| D | 17.5% DMSO ± 17.5% PG | 7 | 3.6 ± .3 | .001 | C |
| E | 20% DMSO + 20% PG | 6 | 2.0 ± .2 | .01 | D |
| F | 40% DMSO | 7 | 1.2 ± .2 | .01 | E |
| G | 40% DMSO, Introduced at −20° C. | 5 | 2.6 ± .1 | .001 | F |
| H | 22.8% DMSO ± 17.2% Acetamide | 7 | 3.2 + .4 | .001 | F |
| I | 11.4% DMSO + 8.6% Acetamide + 20% PG | 7 | 2.8 ± .2 | .05 .001 | E F |
| J | Controls | 5 | 5.2 ± .3 | — | — |
| K | 22.8% DMSO + 17.2% Acetamide | 5 | 4.1 ± .4 | .03 | J |
| L | 30% DMSO + 10% Urea | 4 | 4.4 ± .5 | NS | J,K |
| M | 13.3% DMSO + 13.3% Acetamide + 13.4% PG | 7 | 3.3 ± .1 | .05 | K |
| N | 10% DMSO + 10% Acetamide 10% PG + 10% EG | 6 | 3.3 ± .2 | NS | M |
| O | 8% DMSO + 8% Acetamide + 8% PG + 8% EG + 8% Glycerol | 6 | 3.6 ± .1 | NS | M,N |

*All experiments conducted at 0° C. unless otherwise noted. All samples were exposed to the indicated glass-forming solution for 40 minutes. Samples in the top portion of the Table were exposed to 20% glass-former for 30 min and to 30% glass former for 60 min before the introduction of the final concentration. Samples in the bottom portion of the Table were exposed to 20% glass-former for 60 min and to 30% glass-former for 30 min before the introduction of the final concentration. All samples were treated with 10% glass-former for 30 min prior to exposure to 20% glass-former. All experiments were carried out at atmospheric pressure.

Figure 3:
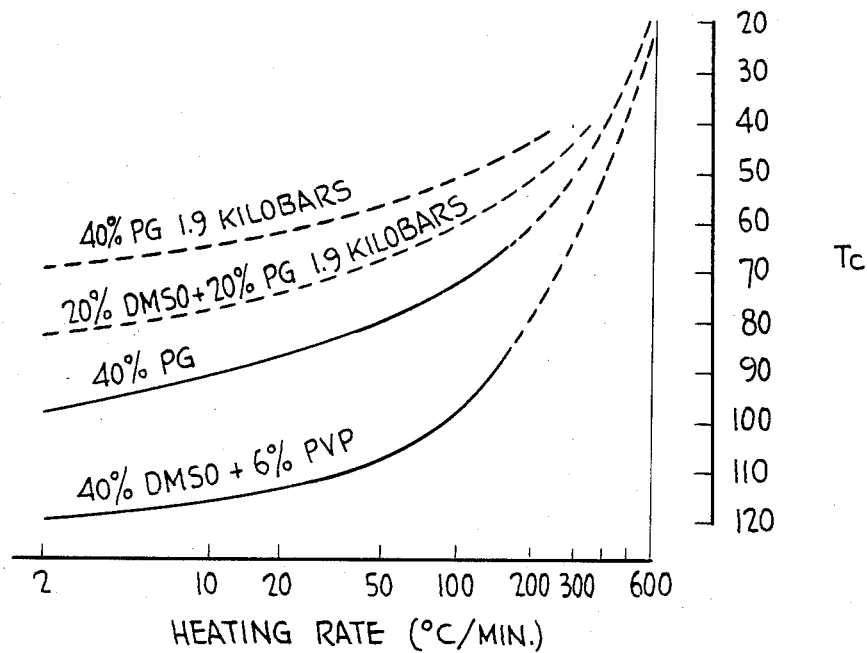
Figure 4:
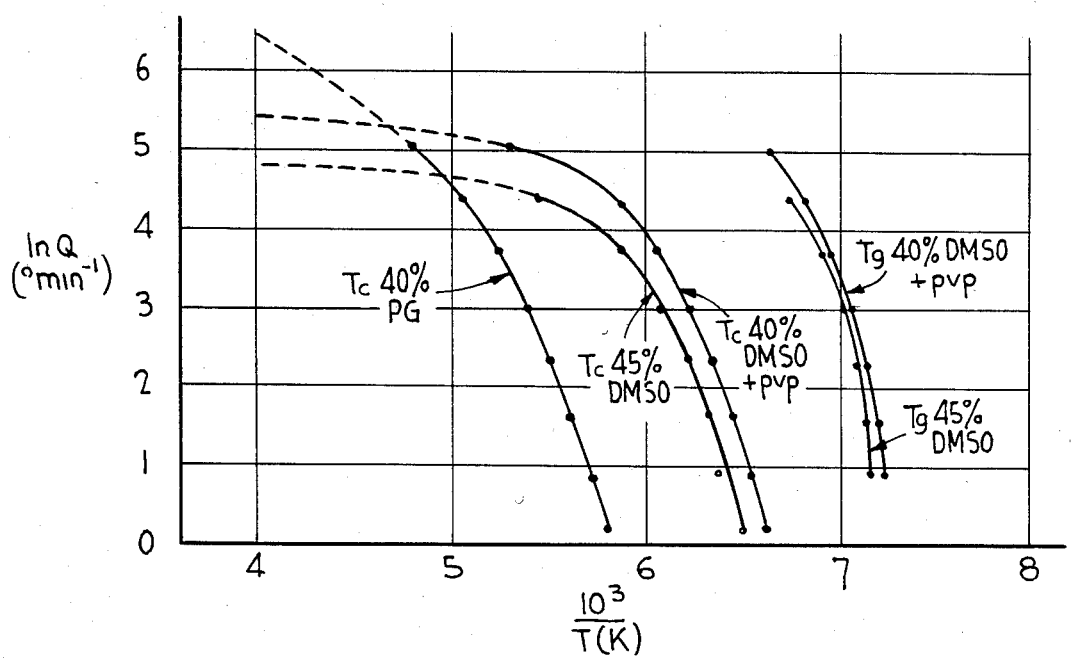

A serious obstacle to organ preservation by vitrification is devitrification, or crystallization during warming. Devitrification can be impeded by increasing the warming rate, by increasing the pressure, by increasing the penetrating solute concentration, and by including polymers such as PVP or similar non-penetrating low molecular weight solutes. Some studies of devitrification are shown in FIG. 3. By extrapolation, 40% PG and 40% DMSO+6% PVP require warming rates on the order of 600° C./min to prevent devitrification at temperatures equal to the melting points of these solutions at normal atmospheric pressure. This rate may well be achievable using state-of-the-art microwave warming technology developed for thawing of dog and rabbit kidneys. However, the application of 1900 atm elevates the devitrification temperature ($T_c$) by 30° C. at lower cooling rates and depresses the liquidus temperature ($T_m$) (melting point) by about 20° C., which generally prevents devitrification at warming rates on the order of only 200°–300° C./min. With the addition of PVP, the critical warming rate is reducible to about 100° C./min, which is a rate currently achievable for frozen kidneys. Although 1.9 kbar is currently damaging to kidney tissue, damage is not contemplated if applied only below −20° C. and if applied for only 15 or 20 seconds. The rate of devitrification of more dilute solutions is considerably greater than the rate of devitrification of 40% solutions, and for this reason devitrification may impose a lower limit on the necessary glass-forming concentration for vitrification, if recovery of the biomaterial is desired. However, the limiting penetrating GF level is that compatible with vitrification when avoidance of devitrification is not relevant, for example in studies of cellular ultra-structure, rather than for viable cell preservation.

BEST MODE PROCEDURE

The biological system is first slowly equilibrated with a 10% to 25% (w/v) vitrification solution at temperatures in the vicinity of 0° C. (±10° C.), or higher if toxicity is not a problem. The concentration is then changed in one step to 35%–50% (the concentration required to vitrify), until the system becomes vitrifiable (cells need not and generally should not be allowed to return to their isotonic volumes). At an appropriate time the system is placed into a high pressure chamber and as soon as it has equilibrated sufficiently to vitrify with the aid of high pressures, the pressure is rapidly raised to 500–2000 atm and the temperature lowered as quickly as possible to below −130° C., the glass transition temperature at room pressure. Once the center of the system reaches −130° C. to −145° C., but not lower, further cooling must be prevented to prevent cracking of the glass. The pressure is slowly released and the system is cooled at a rate no higher than, and often much more slowly than, 0.5° C./min, with or without a period of "annealing" at about −140° C. to permit the fictive temperature to reach the holding temperature and relieve mechanical stresses. Cooling should be done in a container with no rigid walls or without a container other than a "coat" of glassy solution surrounding the system. Storage should be at temperatures between about −150° C. and −200° C. To retrieve the system from storage, it should be warmed very slowly to near $T_g$, repressurized if necessary, and warmed as rapidly as possible to temperatures approaching $T_m$, using microwave or induction heating if necessary. (Attempts to rapidly heat from lower temperatures will tend to result in shattering of the glass.) At this point the pressure, if any, is released and, upon reaching 0±10° C., the system is immediately perfused with or otherwise exposed to a 15–30% w/v solution of PGF, plus an osmotic antagonist such as mannitol to control any cellular swelling, and the concentration is then gradually brought to zero and the system used for the intended purpose.

Particularly useful exemplary vitrification solution compositions are as follows: mixtures of 17.5% DMSO, 17.5% propylene glycol, and 6% PVP (41% total concentration) which form doubly unstable glasses. Mixtures of approximately 12.8% DMSO, 12.8% propylene glycol, and 19.4% acetamide (AA), and 6% PVP (total concentration, 51%) are so stable that no devitrification is observed during warm-up at approximately 5° C./min, at 1 atm, and no pressurization is required for vitrification. For most organs, a concentration of about 46–49% DMSO-PG-AA-PVP will be suitable, especially a solute system comprising about 18.22% w/v DMSO, 13.78% w/v acetamide, 10% w/v propylene glycol, and 6% w/v PVP K30, in appropriate base solution. The concentration of DMSO and acetamide may vary from about 25% to 35% depending on pressure and the concentration of PG and PVP.

Variations on the exemplified methods are contemplated. Pressure can be applied simultaneously with cooling, or in steps as temperature is changed, to minimize injury. Systems can be equilibrated at lower temperatures than exemplified to reduce solute toxicity, if necessary. For cells, the protective solutions may be emulsified to minimize effects of any heterogeneous nucleation.

What is claimed is:

1. An improved method for the cryopreservation of biological materials wherein the biological material is cooled to a vitreous state under pressure in the presence of an aqueous vitrification solution containing penetrating glass-forming solutes, the improvement comprising (a) replacing a sufficient amount of said penetrating solute in said solution with an equivalent amount of non-penetrating glass-forming solute to reduce damage to the biological material when exposed thereto; (b) treating the biological material with the solution obtained from step (a) at a rate and duration sufficient to prevent cells in said biological material from returning to isotonic volume prior to vitrification; and (c) then subjecting the biological material to a pressure sufficient for vitrification upon cooling without substantial nucleation or ice crystal growth and without significant injury to the biological material.

2. The method of claim 1, wherein said biological material is an organ or a tissue.

3. The method of claim 2, wherein the organ is a kidney, heart, or liver.

4. The method of claim 1, wherein the vitrification solution comprises dimethyl sulfoxide, propylene glycol, and polyvinylpyrrolidone (PVP).

5. The method of claim 4, wherein the vitrification solution further includes a blocking compound which counters the toxicity of dimethyl sulfoxide.

6. The method of claim 5, wherein the blocking compound is an amide.

7. The method of claim 6, wherein the amide is acetamide.

8. The method of claim 1, wherein the aqueous solution has a solute concentration of penetrating glass-former of from about 30% w/v to about 55% w/v.

9. The method of claim 8, wherein said concentration ranges from about 41 to about 55% w/v.

10. The method of claim 1, wherein the intracellular volume of the cells of the biological material is from about one-third to two-thirds of the isotonic volume during vitrification.

11. The method of claim 8, wherein the cells of the biological material are not fully permeated with vitrification solution prior to vitrification.

12. The method of claim 1, wherein the pressure is below about 2000 atm.

13. The method of claim 12, wherein the pressurization rate is at or below about 500 atm/min, and the cooling rate is at or below about 100° K./min.

14. The method of claim 13, wherein the solution is vitrification at about 1200 atm or lower.

15. The method of claim 1, wherein the biological material is an organ which is perfused with solution at temperatures from about −10° C. to about +10° C. prior to application of pressure.

16. The method of claim 1, wherein the non-penetrating glass-forming solute is polyvinylpyrrolidone.

17. The method of claim 1 wherein the non-penetrating glass-forming solute is present at a concentration of about 6% w/v.

18. The method of claim 1 wherein the non-penetrating glass-forming solute is selected from the group consisting of hydroxyethyl starch, Haemaccel, sucrose, proteins and colloids.

* * * * *